(12) United States Patent
Gonda et al.

(10) Patent No.: US 11,839,539 B2
(45) Date of Patent: Dec. 12, 2023

(54) VALVE SEALING TISSUE AND MESH STRUCTURE

(71) Applicant: EDWARDS LIFESCIENCES CORPORATION, Irvine, CA (US)

(72) Inventors: Edward L. Gonda, Minneapolis, MN (US); Sinatha Sok, Roseville, MN (US)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 480 days.

(21) Appl. No.: 15/977,842

(22) Filed: May 11, 2018

(65) Prior Publication Data

US 2018/0325664 A1 Nov. 15, 2018

Related U.S. Application Data

(60) Provisional application No. 62/506,480, filed on May 15, 2017.

(51) Int. Cl.
*A61F 2/24* (2006.01)

(52) U.S. Cl.
CPC .......... *A61F 2/2418* (2013.01); *A61F 2/2409* (2013.01); *A61F 2/2412* (2013.01); *A61F 2/2427* (2013.01); *A61F 2/2442* (2013.01); *A61F 2230/0069* (2013.01); *A61F 2250/0063* (2013.01)

(58) Field of Classification Search
CPC ..... A61F 2/2418; A61F 2/2409; A61F 2/2412
See application file for complete search history.

(56) References Cited

U.S. PATENT DOCUMENTS

| 4,473,423 | A | 9/1984 | Kolff | |
|---|---|---|---|---|
| 6,582,464 | B2 | 6/2003 | Gabbay | |
| 9,034,032 | B2 * | 5/2015 | McLean | A61F 2/2409 623/2.12 |
| 9,271,831 | B2 * | 3/2016 | Thill | A61F 2/06 |
| 2003/0109922 | A1 * | 6/2003 | Peterson | A61F 2/2409 623/2.4 |
| 2005/0203617 | A1 | 9/2005 | Forster et al. | |
| 2006/0271166 | A1 | 11/2006 | Thill et al. | |
| 2012/0065728 | A1 | 3/2012 | Gainor et al. | |
| 2013/0304200 | A1 * | 11/2013 | McLean | A61F 2/2412 623/2.18 |
| 2014/0214159 | A1 | 7/2014 | Vidlund et al. | |
| 2015/0066140 | A1 | 3/2015 | Quadri et al. | |

OTHER PUBLICATIONS

European Patent Office, Supplementary European Search Report dated Apr. 7, 2020 in European Patent Application No. 18802714, 7 pp.
WIPO, U.S. International Search Authority, International Search Report and Written Opinion dated Aug. 1, 2018 in International Patent Application No. PCT/US2018/032403, 9 pages.

* cited by examiner

*Primary Examiner* — Megan Y Wolf

(57) ABSTRACT

A prosthetic valve device that includes multiple layers and liners attached to various locations on the layers to prevent paravalvular leakage.

5 Claims, 3 Drawing Sheets

VALVE SEALING TISSUE AND MESH STRUCTURE

RELATED APPLICATIONS

This application claims priority to U.S. Provisional Application Ser. No. 62/506,480 filed May 15, 2017 entitled Valve Sealing Tissue And Mesh Structure, which is hereby incorporated herein by reference in its entirety.

BACKGROUND OF THE INVENTION

Transcatheter valve repair devices and valves are useful in repairing or replacing defective cardiac valves, typically using a catheter delivery system. One complication that can arise with prosthetic valves is paravalvular leakage, which is blood flowing around the valve, rather than through the valve. This can result when the valve is not properly seated in the native valve annulus, or when there is a pathway for blood to flow between the leaflets of the prosthetic valve and the anchoring structure used to support the prosthetic valve leaflets. The former cause is mitigated through proper valve placement and sizing. The latter form of leakage, however, is typically a result of a design flaw or defective valve mechanism. The present invention is directed toward an improved valve design that reduces or eliminates paravalvular leakage.

OBJECTS AND SUMMARY OF THE INVENTION

One aspect of the invention provides a prosthetic valve design, such as a cardiac valve design, that reduces paravalvular leakage. Leakage is reduce by associating a tissue liner with a mesh support structure. The tissue liner may be preferred over other liners as tissue is impermeable to fluid flow.

Another aspect of the invention provides a tissue liner that sits between a middle and outer layer of a mesh valve support.

Yet another aspect of the invention provides a tissue liner that is attached to an outer layer of a mesh valve support with at least one suture.

Still another aspect of the invention is a prosthetic valve that includes a support structure having a delivery configuration and a delivered configuration, wherein in the delivery configuration the support structure takes the form of an elongated tube, and in the delivered configuration, the support structure folds to take on a form that includes: an outer layer; a middle layer; and an inner layer. The valve device further includes a valve assembly attached to the inner layer of the support structure and including: a wireform that has commissural points and a valve material attached to the wireform to create valve leaflets, said valve material extending from the commissural points of the wireform to form a valve skirt attached to the middle layer of the support structure. The valve device also has an outer liner attached to an inside surface of the outer layer of the support structure.

In another aspect of the invention, the device also has a tissue ring attached to the middle layer of the support structure.

In yet another aspect of the invention, the device has a valve skirt is attached to an outside surface of the middle layer of the support structure. The valve skirt may alternatively be attached to an inside surface of the middle layer of the support structure.

In one aspect of the invention, the support structure comprises a mesh tube.

In another aspect, the outer layer comprises a flared section, an upright section extending from the flared section, a tapered section extending from the upright section, and a first folded section.

In still another aspect of the invention, the outer liner is attached to the flared section of the outer layer.

In another aspect of the invention, the support structure comprises a braided wire tube with gaps being defined by the braided wire and said outer liner protrudes through the gaps.

One aspect of the invention provides a method of preventing paravalvular leakage through a prosthetic valve. The method generally includes the steps of providing a prosthetic valve with a support structure having an outer layer and lining an inside surface of the outer layer with a tissue liner.

In one aspect of the method of the invention, the step of lining the inside surface of the outer layer with a tissue liner comprises lining the inside surface of the outer layer with a tissue liner that protrudes through gaps formed in the support structure.

In another aspect of the method of the invention, the step of providing the prosthetic valve with the support structure having the outer layer comprises providing the prosthetic valve with the support structure having the outer layer, a middle layer, and an inner layer.

In yet another aspect of the invention, the method further comprises attaching a tissue ring to the middle layer.

In still another aspect of the method of the invention, the step of providing the prosthetic valve with the support structure having the outer layer further comprises: providing the prosthetic valve with a valve assembly including a length of valve material that is attached to a wireform and extends past the wireform; and attaching the material that extends past the wireform to at least the middle layer of the support structure.

The method of the invention may further comprise attaching the material that extends past the wireform to the inner layer of the support structure.

In one aspect of the method of the invention, the step of attaching the material that extends past the wireform to the inner layer of the support structure comprises attaching the material that extends past the wireform to an inside surface of the inner layer of the support structure. Alternatively, the step of attaching the material that extends past the wireform to the inner layer of the support structure comprises attaching the material that extends past the wireform to an outside surface of the inner layer of the support structure.

Another aspect of the invention is a prosthetic valve device that includes a support structure having a plurality of layers including at least an outer layer and an inner layer; a valve assembly connected to the inner layer; and a tissue liner lining an inside surface of the outer layer. The valve assembly may include a tissue skirt attached to an inside or outside surface of said inner layer.

Yet another aspect of the invention is a prosthetic valve device with a plurality of layers including a middle layer with a tissue ring attached to a surface thereof.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which.

DESCRIPTION OF EMBODIMENTS

Figure 1:
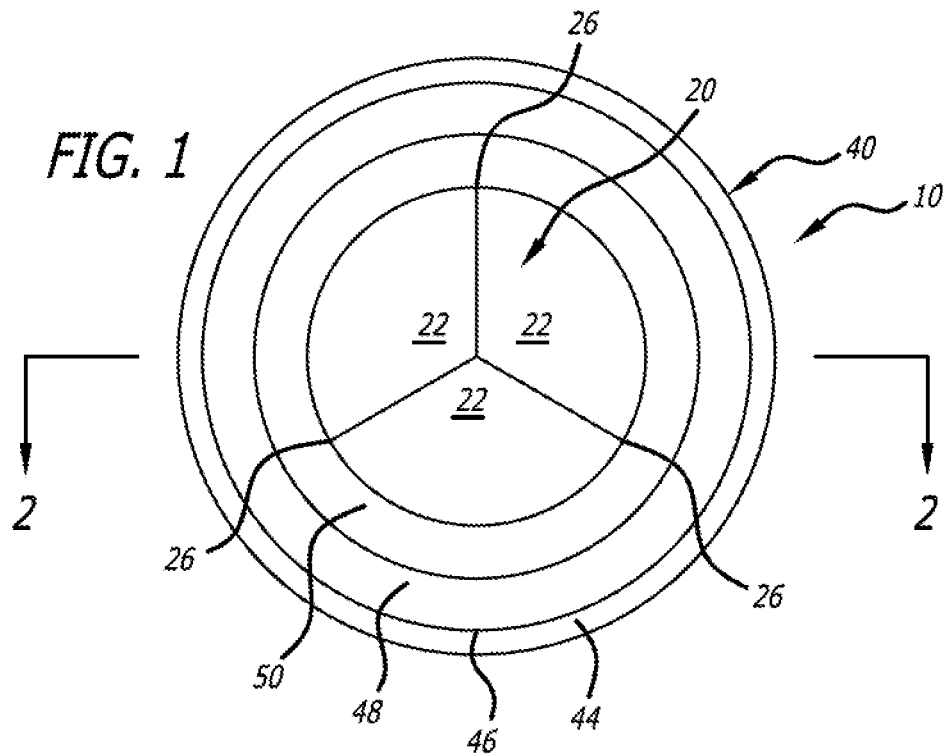
FIG. 1 is a plan view of an embodiment of a device of the invention.
Figure 2:
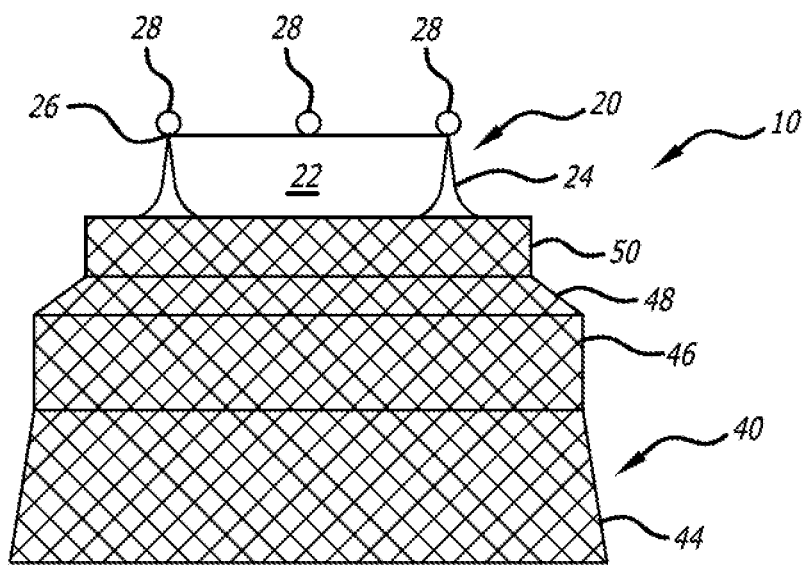
FIG. 2 is an elevation of an embodiment of a device of the invention.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

Referring now to the figures there is shown an embodiment of a prosthetic valve 10 of the invention. Valve 10 generally includes a valve assembly 20 and a support structure 40. The valve assembly 20 includes valve leaflets 22 supported by a wireform 24, which forms commissures 26. The commissures 26 may include loops 28 for purposes of implantation and retrieval. The valve leaflets 22 may be formed from natural tissue, such as porcine tissue. However, synthetic materials may also be used without departing from the spirit of the invention.

Figure 3:
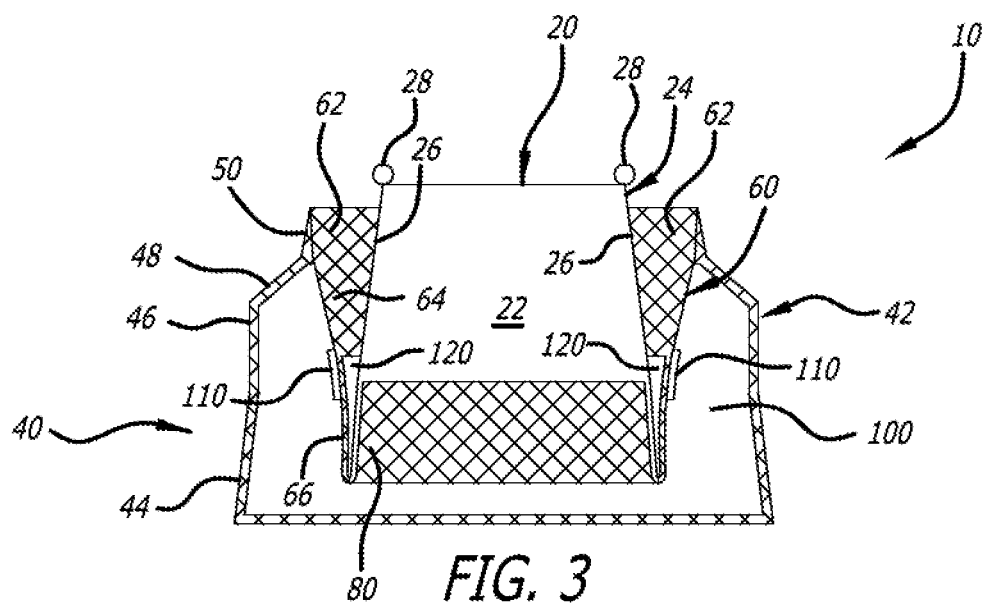
FIG. 3 is a sectional view of the embodiment of FIG. 1 taken along section lines A-A.
Figure 4:
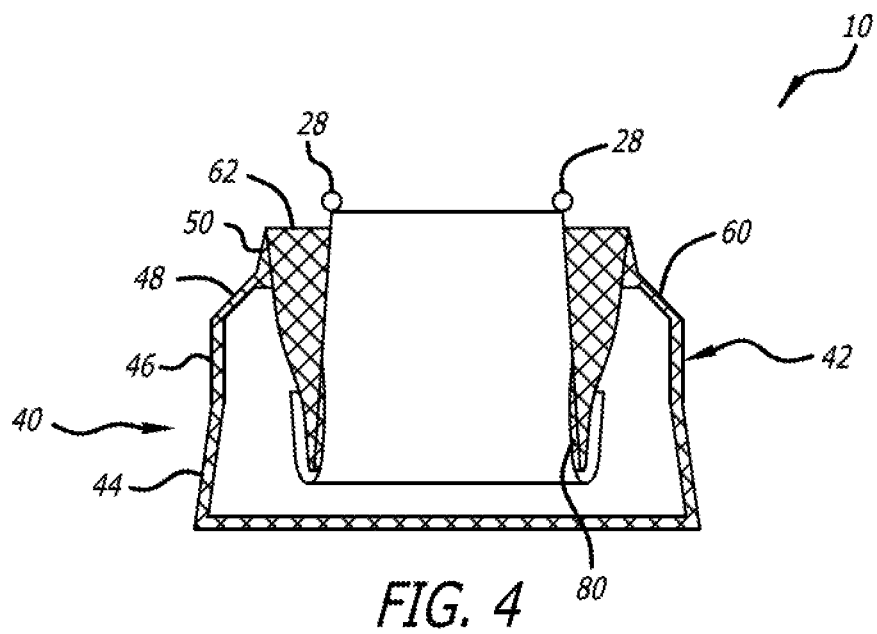
FIG. 4 is a sectional view of an embodiment of the invention from a similar perspective as FIG. 3.

The support structure 40 may be formed from a tube of material such as a braided mesh, or may be a fenestrated structure cut from a solid tube. Good results have been obtained using a memory metal mesh braid. The structure 40 includes several layers that are bordered by folds or creases. Specifically, there is an outer layer 42, a middle layer 60, and an inner layer 80. Middle layer 60 and inner layer 80 are shown in FIGS. 3 and 4.

The outer layer 42 includes various sections that give it a shape suitable for nesting in a native valve annulus, such as a cardiac valve. This shape aids in its ability to prevent paravalvular leaking, as well as ensuring the valve 10 will not migrate after implantation. In one embodiment, the outer layer includes a flared section 44 that leads to an upright section 46, followed by a tapered section 48 and a first folded section 50. One skilled in the art will realize that the transitions between sections 44, 46, and 48 may be angular creases, as shown, or may be gradual curved transitions. Moreover, the shape of the outer layer 42 may vary without departing from the scope of the invention.

The middle layer 60 includes a second folded section 62 that continues from the first folded section 50 of the outer layer 42. The second folded section 62 leads into an angled section 64, which continues to a third folded section 66.

The inner layer 80, in the embodiment shown in the figures, continues from the third folded section 66 and does not necessarily include multiple sections.

Paravalvular leakage is prevented, in part, by strategic placement of material on the various section of the support structure 40. In a first embodiment, shown in FIG. 3, includes three protective liners. An outer liner 100 is sewn into the inside surface of the outer layer 42. Specifically, the outer liner 100 spans the flared section 44 and may extend up into the upright section 46 and tapered section 48. All of the liners described herein are preferably circumferential. Non-limiting examples of tissue liner materials include: bio-expandable materials, impermeable fabric, compliant polymers, molded polymers, and hydrogels. It has been found that an impermeable tissue liner performs superiorly in comparison to a woven polyester liner by preventing blood flow through the outer layer 42 of the support structure 40. Furthermore, in all embodiments, fabric may be adhered to the tissue liners to encourage further ingrowth of native tissue.

The outer tissue liner 100 is attached to the outer layer 42 of the mesh valve support and the second liner 110 is attached to the middle layer 60 of the mesh valve support. The tissue liner 100 may be designed to protrude through the outer layer 42 of the support structure 40 to form a seal against the native valve annulus. Providing a tissue liner on the inside surface of the support structure may be advantageous to placement on the outside surface of the support structure 40 in that the wire of the support structure is now in contact with the native tissue, providing a higher friction coefficient than a tissue-covered stent. Furthermore, during valve loading and delivery, the wire mesh provides a barrier between the relatively delicate tissue and the stent, minimizing the risk of damaging the tissue layer.

Sealing is enhanced by the tissue protruding through the gaps in the support structure in use. Varying the thickness of the liner, and/or the size of the gaps of the support structure, will provide different degrees of protrusion. The protrusion effect can be further enhanced by forming the middle layer 60 to have elbows that act on the inside surface of the liner 100 to push it through the outer layer 42.

The second liner 110 may be in the form of a tissue ring and may be sewn through the middle layer 60 of the mesh support 40 to make intimate contact with the tissue skirt coming off the valve leaflets, described below. Specifically, the tissue ring 110 is located on an outer surface of the middle layer 60 on the angled section 64, and may extend onto the third folded section 66. The tissue ring 110 may include bio expandable materials, impermeable fabric, compliant polymers, molded polymers, and hydrogels, just to name a few non-limiting examples.

The tissue ring 110 enhances the sealing between the mesh layers by compressing against the tissue liners in between the layers of mesh, acting like a gasket or an o-ring. Different annulus sizes alter the height of the valve and can alter the location of the mating surfaces. As such, the tissue ring 110 is adaptable to many annulus sizes with the same mesh structure since the ring 110 is smaller than the tissue liner 100 and can align itself anywhere along the length. The tissue ring 110 may be made, in conjunction with the mesh density, to match the diamond pattern of the middle layer 60 to enhance protrusion through the mesh gaps. The tissue ring 110 may be attached to the middle layer 60 using a variety of means. Non-limiting examples include: suture knots, running suture stitches, metal crimps, adhesive, cauterization, and laser adhesion.

The third liner, the inner liner 120, is an extension, or skirt, of the valve leaflets 22. In a first embodiment, shown in FIG. 3, the extra material of the valve leaflets 22, forming the inner liner 120, extends into the fold between the third folded section 66 of the middle layer 60 and the inner layer 80.

In a second embodiment, shown in FIG. 4, the extra material of the valve leaflets 22, forming the inner liner 120, is routed to an inside surface of the inner layer 80, and wraps around the third folded section 66 of the middle layer 60.

Each of the embodiments of the device 10 described herein has a delivery configuration and a deployed configuration. In the delivery configuration, the folds are straightened and the mesh support structure is in the form of an elongated tube. The liners are attached to the support structure such that, upon folding, the liners are appropriately placed.

Figure 5:
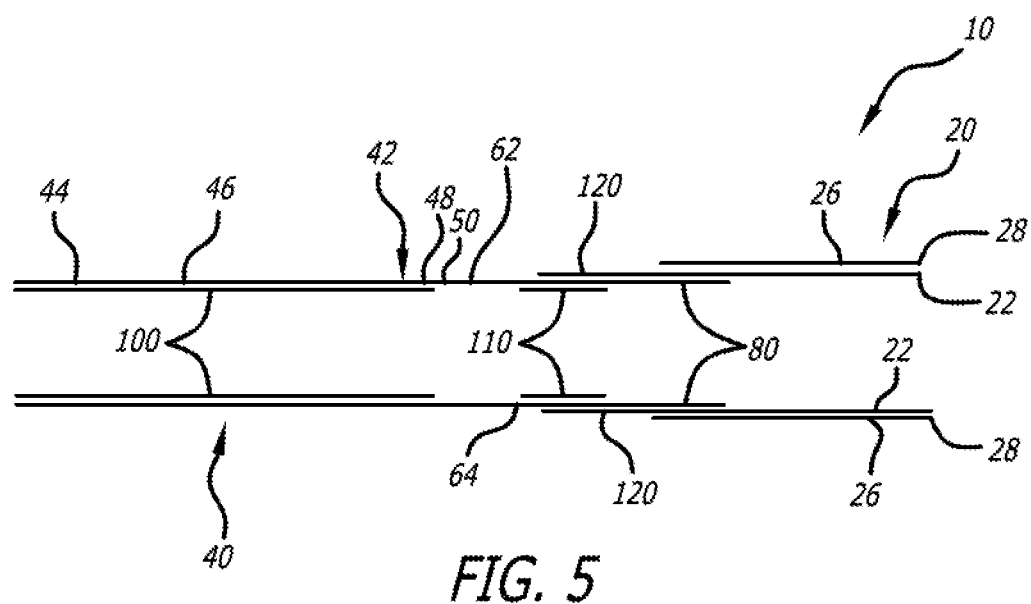
FIG. 5 is a cutaway view of the device of FIG. 3 in an extended, delivery configuration; and, FIG. 6 is a cutaway view of the device of FIG. 4 in an extended, delivery configuration.

The delivery configuration of the embodiment of FIG. 3 is shown in FIG. 5. FIG. 5 shows that in the delivery configuration, support structure 40 is a continuous tube that includes layers 42, 60 and 80. When extended the order, moving from left to right as shown, of the various sections and layers becomes outer layer 42, with sections 44, 46, 48 and 50. Liner 100 is contained within the support structure 40 and generally aligned with the outer layer 42. Next is middle layer sections 62, 64 and 66. Tissue ring 110 is attached to the inner surface of the support structure 40 at the tapered section 64 of the middle layer 60. The support structure 40 terminates with the inner layer 80. The wireform 24 is attached on an outside surface of the support structure 40 at the inner layer 80. The valve tissue 22 is attached to the wireform 24 and includes the skirt that forms the inner liner 120. The tissue 22 thus extends past the end of the wireform and along the outside surfaces of the inner layer 80 and middle layer 60.

Figure 6:
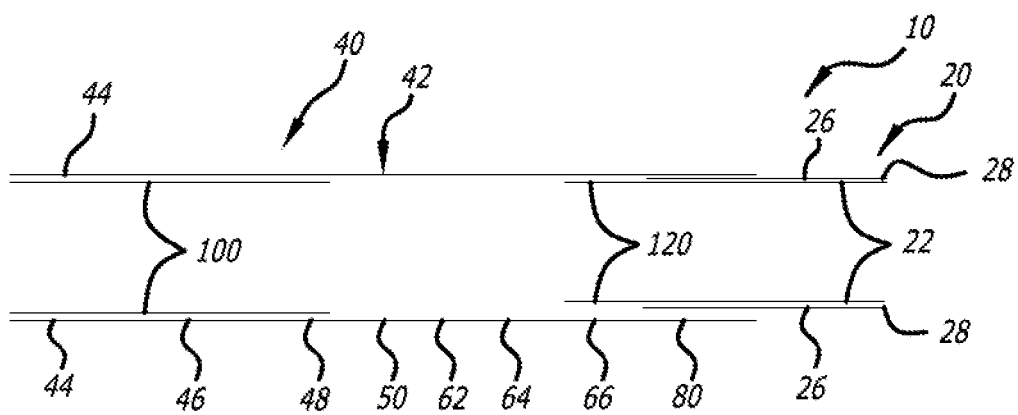

The delivery configuration of the embodiment of FIG. 4 is shown in FIG. 6. FIG. 6 differs from FIG. 5 in that there is no tissue ring 110 (optionally) and the inner liner 120 and wireform 24 are routed on the inside of the support structure 40. As such, FIG. 6 shows that in the delivery configuration, support structure 40 is a continuous tube that includes layers 42, 60 and 80. When extended the order, moving from left to right as shown, of the various sections and layers becomes outer layer 42, with sections 44, 46, 48 and 50. Liner 100 is contained within the support structure 40 and generally aligned with the outer layer 42. Next is middle layer sections 62, 64 and 66. The support structure 40 terminates with the inner layer 80. The wireform 24 is attached on an inside surface of the support structure 40 at the inner layer 80. The valve tissue 22 is attached to the wireform 24 and includes the skirt that forms the inner liner 120. The tissue 22 thus extends past the end of the wireform and along the inside surfaces of the inner layer 80 and middle layer 60.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A prosthetic valve comprising:
   a support structure having a delivery configuration and a delivered configuration, wherein in the delivery configuration the support structure takes the form of an elongated tube, and in the delivered configuration, the support structure folds to take on a form that includes:
   an outer layer;
   a middle layer; and
   an inner layer;
   a valve assembly including:
   a wireform including commissural points that extend beyond a proximal end of the support structure, and including a distal end that connects the valve assembly to the inner layer of the support structure;
   valve material attached to the wireform to create valve leaflets, said valve material extending from the commissural points of the wireform beyond a first fold of the support structure to form a valve skirt;
   wherein the valve skirt is attached to the middle layer of the support structure;
   an outer liner attached to an inside surface of the outer layer of the support structure; and
   a tissue ring attached to the middle layer of the support structure.

2. The prosthetic valve of claim 1 wherein said valve skirt is attached to an inside surface of the middle layer of the support structure.

3. The prosthetic valve of claim 1 wherein said support structure comprises a mesh tube.

4. The prosthetic valve of claim 1 wherein said outer layer comprises a flared section, an upright section extending from the flared section, a tapered section extending from the upright section, and a first folded section.

5. The valve prosthesis of claim 4 wherein the outer liner is attached to the flared section, the upright section and the tapered section of the outer layer.

* * * * *